(12) United States Patent
McCoy et al.

(10) Patent No.: US 6,495,120 B2
(45) Date of Patent: Dec. 17, 2002

(54) FORMULATION AND SYSTEM FOR INTRA-ORAL DELIVERY OF PHARMACEUTICAL AGENTS

(76) Inventors: Randall McCoy, 10 High Ct., Little Falls, NJ (US) 08551; Robert O. Williams, III, 4514 Rapid Springs Cove, Austin, TX (US) 78746; Miles A. Libbey, III, 2 Blue Spruce Dr., Pennington, NJ (US) 08534

( * ) Notice: Subject to any disclaimer, the term of this patent is extended or adjusted under 35 U.S.C. 154(b) by 0 days.

(21) Appl. No.: 09/944,492

(22) Filed: Aug. 30, 2001

(65) Prior Publication Data

US 2002/0055496 A1 May 9, 2002

Related U.S. Application Data

(63) Continuation of application No. 09/502,871, filed on Feb. 11, 2000.
(60) Provisional application No. 60/119,923, filed on Feb. 12, 1999.

(51) Int. Cl.[7] .............................. A61K 9/12; A61K 9/10; A61K 38/10; A61K 38/28
(52) U.S. Cl. ............................. 424/45; 424/43; 514/2; 514/3; 514/4
(58) Field of Search ........................ 424/45, 43; 514/2, 514/3, 4

(56) References Cited

U.S. PATENT DOCUMENTS 5,011,678 A * 4/1991 Wang et al. .................. 424/45
5,047,230 A * 9/1991 Nagy et al. ................... 424/45
5,288,498 A * 2/1994 Stanley et al. ............... 424/440

OTHER PUBLICATIONS

Aungst et al, Comparison of the effects of various transmucosal absorption promoterson buccal insulin delivery, International Journal of Pharmaceutics, 1989, pp. 227–235.*

Senel et al, Drug permeation enhancement via buccal route: possibilities and limitations, Journal of Controlled Release 2001, pp. 133–144.*

* cited by examiner

Primary Examiner—Jose' G. Dees
Assistant Examiner—M. Haghighatian
(74) Attorney, Agent, or Firm—Mathews, Collins, Shepherd & McKay, P.A.

(57) ABSTRACT

A stable formulation is disclosed that enables the effective intra-oral delivery to a patient of a pharmaceutical agent. The formulation comprises the pharmaceutical agent mixed with an orally-acceptable oral-absorption enhancer in an orally-acceptable carrier-solvent, wherein the oral-absorption enhancer is adapted to modify the surface membrane such that absorption through the surface membrane is initiated or increased. The oral-absorption enhancer may comprise hydroxypropyl-beta-cyclodextrin and surfactants including benzalkonium chloride, benzethonium chloride, polysorbate 80, sodium lauryl sulfate, Brij surfactants, Tween and Pluronic surfactants. Also disclosed is a system for delivering the formulation including a mechanism for dispensing predetermined doses of the inventive formulation intra-orally as with an aerosol or spray pump or propellant device.

27 Claims, 4 Drawing Sheets

FORMULATION AND SYSTEM FOR INTRA-ORAL DELIVERY OF PHARMACEUTICAL AGENTS

RELATED APPLICATIONS

CROSS-REFERENCE TO RELATED APPLICATIONS

This is a continuation of the prior application Ser. No. 09/502,871, filed Feb. 11, 2000.

This application is related to, and claims the benefit of priority under, U.S. provisional patent application Ser. No. 60/119,923, filed Feb. 12, 1999.

FIELD OF THE INVENTION

This invention relates to a formulation effective for the intra-oral delivery of pharmaceutical agents and to a system comprising the formulation in a metered-dose applicator device for dispensing the pharmaceutical agents intra-orally.

BACKGROUND OF THE INVENTION

The poor aqueous solubility and the hydrophobic nature of many therapeutic agents prevent them from being suitable for conventional oral delivery, due to their poor absorption and bioavailability. In other cases, the current means of delivery are primarily limited to parental means, often compromising the desired level of patient compliance. Many small and large molecule proteins and peptides are effective therapeutically, yet are not ordinarily easily absorbed through, or are otherwise not effective when administered through, the GI tract, including insulin, calcitonin, human growth factors, and others.

Difficulties inhere in administering certain pharmaceutical agents orally (such as proteins), as saliva and/or gastrointestinal compounds tend to degrade or digest the pharmaceutical agents, rendering them ineffective. For example, patients suffering from diabetes are required to administer insulin to themselves by injection on a regular basis. Injection delivery of insulin and other drugs is inconvenient and can be painful, discomforting, and embarrassing.

Injectionable drug delivery also may be used to achieve a quick and efficient administration. Chronic pain management is an area where speedy drug delivery is desired. For example, there is a significant increase in the prevalence and number of cancer deaths worldwide. Pain occurs in more than 80% of cancer patients before death. Because of its high frequency, combined with the lack of availability of opioids in many countries and the under-treatment of pain, the World Health Organization in declared pain a world medical emergency in 1986. Since then, emphasis has been on the appropriate treatment of cancer pain. As a result, the use of opioid analgesics has increased worldwide. Fentanyl is an opioid analgesic commonly used in chronic pain management. Currently, research is being conducted which searches for alternative means of quickly and effectively administering this drug.

Efforts to achieve quicker and more convenient methods of drug delivery have involved the development of nasal and pulmonary delivery mechanisms. These delivery mechanisms have been available for a select number of pharmaceutical agents. For example, aerosol delivery systems with various inhalation-actuated aerosol-dispensing devices have been employed for treatment of asthma, and recently they have been investigating for delivery of insulin. Such devices are breath-activated and designed for delivery to the pulmonary system. See, e.g., U.S. Pat. No. 5,544,646 to Lloyd et al., "Systems for the Intrapulmonary Delivery of Aerosolized Aqueous Formulations"; U.S. Pat. No. 5,320,094 to Laube, "Method of Administering Insulin"; and U.S. Pat. No. 4,648,393 to Landis et al., "Breath Activated Medication Spray", all of which are incorporated herein.

There remains a need for improved formulations and methods for delivering pharmaceutical agents to patients. In particular, there is a need for a quick and easy method of administration that may be used effectively for a wide range of pharmaceutical agents and that avoids long-term toxicological effects as experienced with lung delivery.

SUMMARY OF THE INVENTION

The invention comprises a formulation effective for the delivery of pharmaceutical agents through the mucosa of the intra-oral cavity comprising at least one pharmaceutical agent, one or more oral-absorption enhancers, and optionally, one or more solvent carriers, propellants (e.g., where a propellant device is used for delivery), stabilizers, anti-microbial agents, and auxiliary components. The invention further relates to a system for delivering the formulation including a mechanism for dispensing predetermined doses of the inventive formulation intra-orally as with an aerosol or spray pump or propellant device.

BRIEF DESCRIPTION OF THE FIGURES

For a better understanding of the invention, exemplary embodiments are described below, considered together with the accompanying figures, in which.

DETAILED DESCRIPTION OF THE INVENTION

Figure 1:
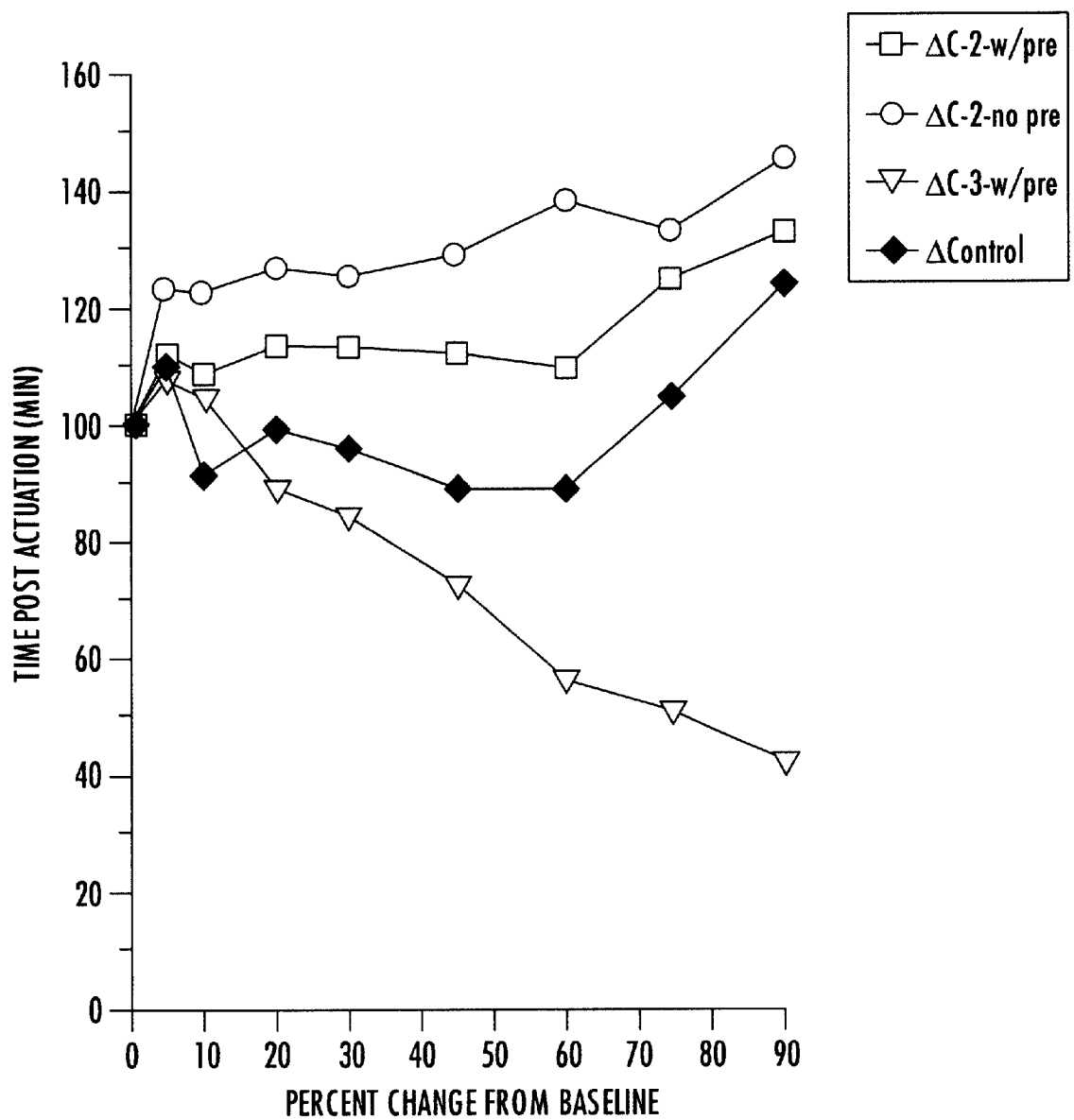
FIG. 1 is a graph showing the effect of inventive formulations containing insulin administered to rats intra-orally wherein plot A reflects application of the invention and plots B,C, and D reflect controls.
Figure 2:
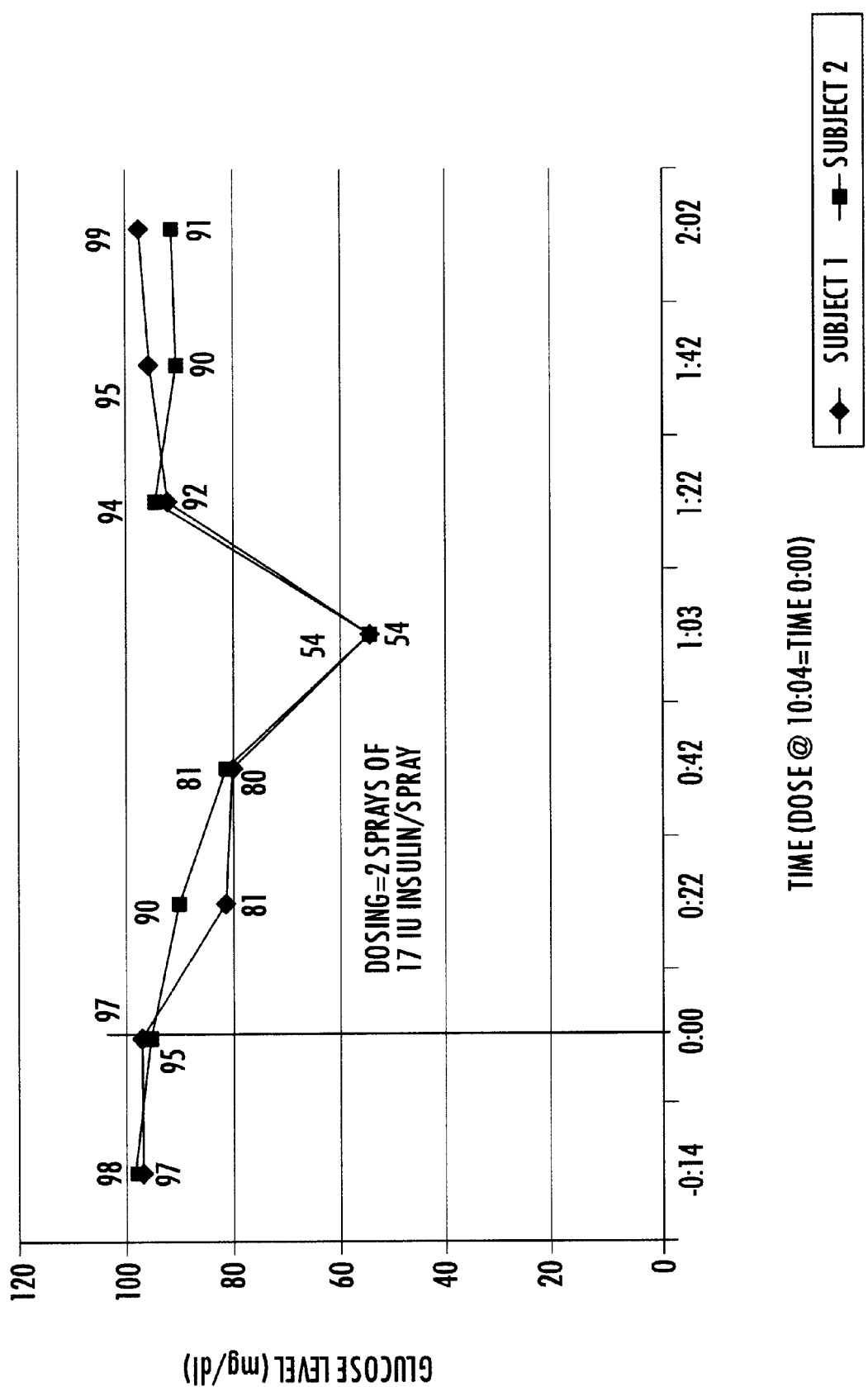
FIG. 2 is a graph showing the effects of inventive formulations containing highly purified porcine insulin administered intra-orally to two human subjects.
Figure 3:
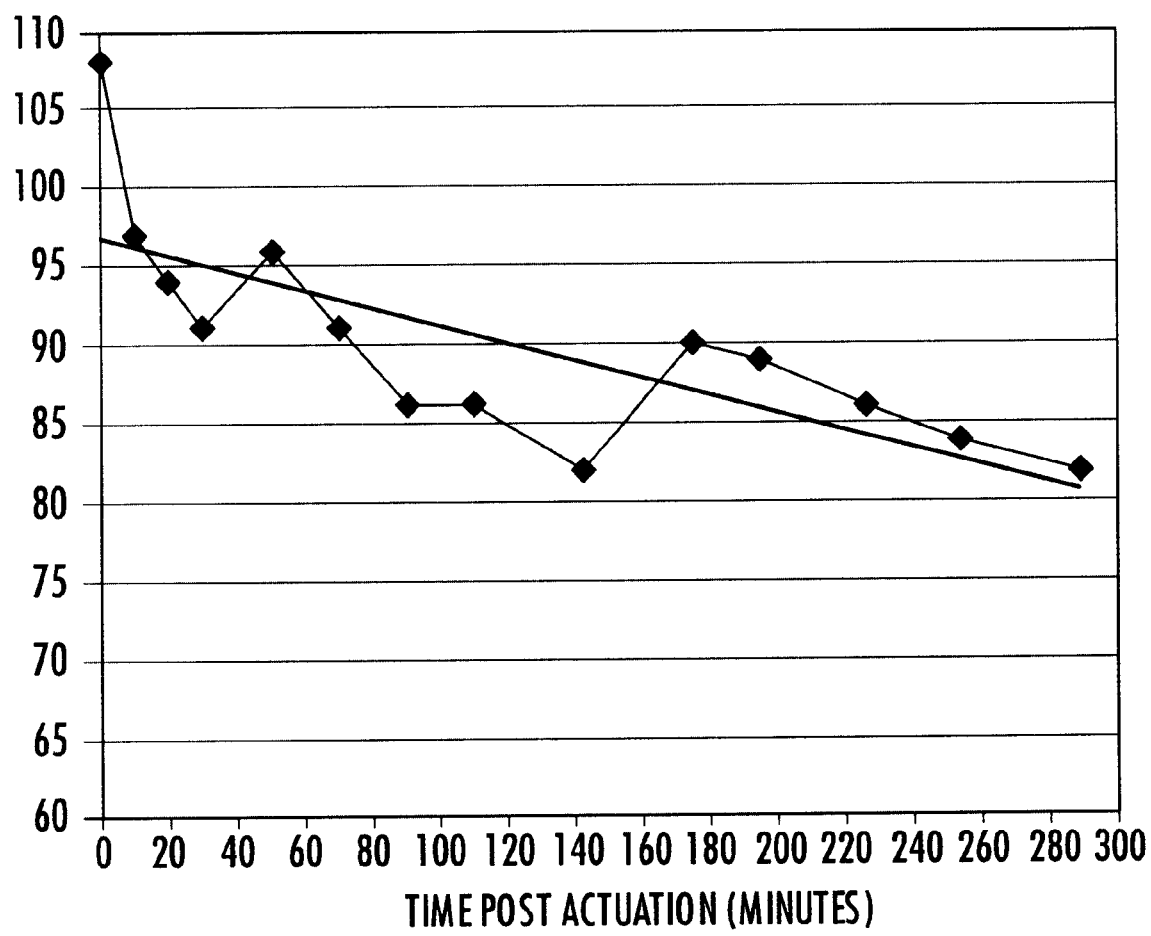
FIGS. 3 and 4 are graphs showing the effects of inventive formulations containing human recombinant insulin administered intra-orally to two human subjects.
Figure 4:
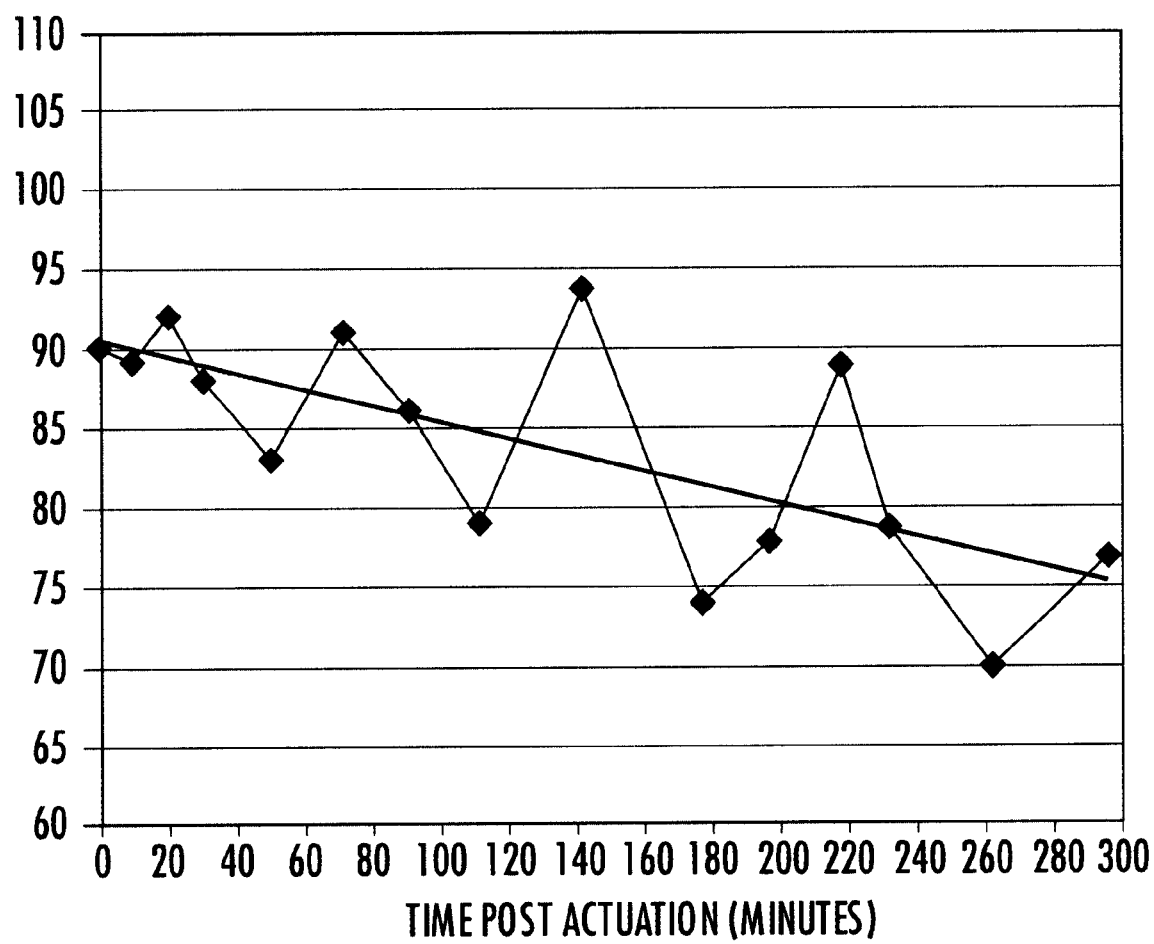

Applicants have discovered a formulation that enables the delivery of pharmaceutical agents through the mucosa of the intra-oral cavity. This target site provides a large surface area and cell membranes with high permeability and significant vascularization for rapid and efficient drug absorption. The formulation of this invention comprises at least one pharmaceutical agent, one or more oral-absorption enhancers, and optionally, one or more solvent carriers, propellants (e.g., where a propellant device is used for delivery), stabilizers, anti-microbial agents, and auxiliary components such as flavor enhancers typically included in orally-administered formulations. The invention further relates to a system for delivering the formulation. The system comprises a mechanism for dispensing predetermined doses of the inventive formulation intra-orally as with a pump or propellant device, which are described further below. The mechanism is referred to as a metered-dose applicator (MDA™), wherein MDA™ is a trademark of MQS, Inc., the assignee of the present application (located in Jamesburg, N.J.).

The invention provides an efficient and convenient drug delivery method for many pharmaceutical agents that results in rapid onset of therapeutic action, avoids the hepatic first pass effect, and reduces the amount of drug needed for an effective doses, thus reducing the cost. With this invention, a noninvasive alternative is provided to pulmonary, nasal, or gastrointestinal delivery of pharmaceutical agents, and absorption is increased and accelerated. The pharmaceutical agent can be directly targeted to the intra-oral delivery site of absorption through the inventive delivery system which combines appropriate droplet size, strength of dose, and absorption enhancers formulated to provide optimum bio-availability and onset of action.

Additionally, the invention is advantageous for therapeutic reasons. The method of delivery described herein is easier, less inconvenient, and/or less-embarrassing than other methods of administration, thus increasing patient compliance. A further benefit of oral versus inhalation administration is that oral spray delivery does not have the same long-term toxicological effects as when inhaling the compounds. The invention also is advantageous in delivering pharmaceutical agents to animals which often are resistant to traditional means of drug delivery. The inventive formulations may be incorporated into morsels including meats or flavor-enhancers to make them more appealing to animals (cats and dogs) to enable their oral delivery.

The formulation of this invention comprises at least one pharmaceutical agent. Suitable pharmaceutical agents for use in the invention include large and small molecular weight compounds, peptides, polypeptides, and proteins. Examples of such compounds include proteins and peptides up to 50,000 Datoms, glucocorticoid steroids, testosterone, dexamethasone, prednisolone, and salts thereof, prednisone, stanozolol, barbituates, seconal and salts thereof, benzodizepines such as flurazepam and salts thereof, miscellaneous sedative hypnotics such as ethchlorvynol and salts. Suitable peptides include hormones such as calcitonin, leuprolide, human growth hormone (HGH), glycogen-like protein (GLP), and salts thereof, and insulin. Various types of insulin may be used, such as bovine, porcine or human-recombinant insulin. Nitroglycerine also may be used, e.g., as a blood pressure medication to counter heart-attacks. Typically, nitro-glycerine is administered in tablet form for delivery under the patient's tongue, but with the instant method of delivery, entry of the agent into the patient's bloodstream is accelerated.

The formulation may comprise one or more analgesics as the pharmaceutical agent. For example, non-narcotic analgesics such as ketorolac and salts thereof, and oxandrolone may be used, or narcotic analgesics, such as morphine, fentanyl and salts thereof, sedative hypnotic agents, and codeine fentanyl citrate. Such analgesic formulations can be used to control pain in cancer patients undergoing chemotherapy who experience debilitating breakthrough pain. Nicotine and related stimulants may also be administered in accordance with the invention.

While concentrations will vary with the particular pharmaceutical agents and formulations used, typically the pharmaceutical agent will be present in the amount of about 0.01 to 25% by weight. For example, embodiments of the formulation comprising use of insulin and fentanyl citrate may comprise use of 0.5% w/w of the pharmaceutical agent.

The inventive formulation further comprises one or more oral absorption enhancers. The term "oral absorption enhancer" is used herein to refer to compounds that disrupt or modify the absorptive surface of the targeted site (such as wetting) to improve absorption across the membrane, either alone or as administered with a metered dose applicator. The term "intra-oral cavity" refers to all areas within the mouth, including the cheeks, gums, lips, tongue, thorax, back of the throat, and beneath the tongue. Typically, the droplet will be sized within the range of about 1 to 200 microns, more preferably within the range of 10–100 microns. The droplets may be presented to the mucosa within a liquid, solid, or gaseous suspension, including an aerosol system which refers to a gaseous suspension of particles dispensed within the form of a mist.

The oral-absorption enhancer may comprise one or more orally-acceptable surfactants or other compounds. The important consideration is that the absorption enhancer be effective for preparing the mucosa to absorb the pharmaceutical agent. Exemplary, suitable oral absorption enhancers include hydroxypropyl-beta-cyclodextrin and surfactants such as benzalkonium chloride, benzethonium chloride, polysorbate 80, sodium lauryl sulfate, Brij surfactants, Tween surfactants, and Pluronic surfactants. Surfactants of the Brij family may comprise polyoxy(n)-oleoether, wherein n is from 1 to 100. Notably, one or more of these and/or other surfactants may be included for other purposes such as increasing the miscibility of the formulation ingredients or reducing the size of the pharmaceutical agents to droplet size. In such case, the surfactant is referred to herein as a "formulation surfactant." As used herein, the term "droplet" refers to a single unit of atomized spray having a sufficiently small size that it is capable of being absorbed by a mucosa of the intra-oral cavity.

While the concentration of oral-absorption enhancers will vary with the particular pharmaceutical agents and/or method of delivery, typically these components will be present in the amount of up to 50% by weight, more preferably in the range of 0.1% to 20% by weight, and even more preferably at about 1±0.5% by weight. For example, exemplary embodiments of the formulation comprise use of sodium lauryl sulfate at 0.9 to 1.2% by weight.

Typically, the formulation will comprise an orally-acceptable carrier solvent. The carrier solvent may include water but preferably is non-aqueous. The phrase "substantially nonaqueous" means that in the nonaqueous solvents used, all reasonable care is used to avoid exposure to atmospheric moisture and remove water present as hydration; however, the presence of small amounts of water in the finished formulation which have no impact on the properties of the formulation can not be precluded. The carrier solvent preferably comprises ethanol, glycerol, glycol, propylene glycol, polyethylene glycol, sorbitol, vitamin E and derivatives of vitamin E, polyvinylpyrrolidone, water, and other orally-acceptable solvents known in the field. Typically, the carrier solvent will be present in an amount of from 0.5 to 50% by weight, more preferably at about 20% by weight.

One embodiment of the invention comprises a system for formulating and delivering desired pharmaceutical agents intra-orally comprising use of a propellant-based assembly, and for such cases, the formulation will comprise use of a propellant. Typically, the propellant will be present in an amount of from 20 to 95% by weight, more preferably at about 50–80% by weight. Various propellants are known in the field and discussed in the literature. However, exemplary propellants comprise carbon dioxide, and hydrofluoroalkane (HFA), which is available from DuPont Corporation, under the tradename HFA 134A™. Also, HFA compounds referred to in the trade as DYMEL™ 152A, HFA 152™, and HFA 227™ advantageously may be used. Such products are known and available in the aerosol industry as earth friendly (green) propellants. Ozone-depleting propellants, such as freone 12, freone 13, butane, and propane, also may be used but are less preferred.

Also optionally included within the compositions are stabilizers and anti-microbial agents. Stability of the pharmaceutical agent over an extended storage period may be aided by stabilizers, such as 1% sodium dodecyl sulfate solution or benzalkonium chloride. Most proteins degrade in the presence of heat. For example, insulin usually must be kept refrigerated to be protected from decomposition. Additionally, the presence of water contributes to the decomposition of pharmaceutical agents by providing a polar vehicle in which the agents can react. Decomposition of the pharmaceutical agents resulting from interaction with water and heat during storage may be reduced by use of stabilizers such as lactic acid, citric acid, and preservative systems including benzoic acid, benzyl alcohol, thimerosal, phenylethyl alcohol, benzethonium chloride, methyl paraben, ethyl paraben, butyl paraben or propyl paraben. When included, stabilizers may comprise up to about 5 weight % of the formulation.

In some forms, such as aqueous-based formulations, anti-microbial agents may be included, as microbial growth may affect the chemical stability of the ingredients, safety and acceptability of the product, and the physical integrity of the system. Lactic acid and citric acid are also exemplary, effective anti-microbial agents. The amount of such agents desirably included will depend upon the particular formulation and can be determined by one skilled in the field with use of micro-organism growth tests.

Optionally, the formulation also may comprise viscosity/mucoadhesive enhancing agents such as cellulose ether polymers and chitosan; flavoring agents; and/or preservative systems including benzoic acid, benzyl alcohol, thimerosal, phenylethyl alcohol, benzethonium chloride, methyl paraben, ethyl paraben, butyl paraben or propyl paraben.

It may include anti-oxidants, kelating agents, preservatives, agents to adjust osmolarity, agents to adjust pH, and non cross-linked polymers.

It will be appreciated that the invention can be used to treat a large variety of diseases, including male hypogonadism, impotence, pain management, diabetes, and osteoporosis, as well as diseases and disorders requiring the administration of small and large molecule proteins and peptides.

The invention further comprises a system for formulating and delivering desired pharmaceutical agents intra-orally comprising use of a mechanism for delivering predetermined doses of the inventive formulation intra-orally, as with a pump or propellant device. Any type of delivery mechanism for administering the formulation intra-orally in metered doses may be used. For example, the formulation can be prepared in a tube (as is used for containing toothpaste) having a nozzle thereon for delivering predetermined units of formulation. Metal, glass, plastic, or other types of containers can be used.

The delivery system or metered dose applicator (MDA™) can be pressurized (pMDA™) or unpressurized (MDA™). Aerosol-type actuators can by used, applying inhalation and pump technology. These actuators may have dual chamber systems that allow for reactive components to be separated until the time of delivery, as is important for some active pharmaceutical products. The applicators may have specialized combination valves to deliver the product adequately and effectively. Thus, the inhalation technology and mechanical configurations for inhalers can be used with the formulations described above to deliver pharmaceutical agents intra-orally, not to the lung. For example, the delivery mechanism may comprise inhalation actuators and nasal actuators sold under the tradenames VALOIS™, BESPAK™, and PFIFFER™. A representative actuator is described in U.S. Pat. No. 5,284,133 to Burns et al., "Inhalation Device with a Dose-Timer, An Actuator Mechanism, and Patient Compliance Monitoring Means," which is incorporated herein.

With the pump applicators, the mechanism will include a container or chamber coupled to a pump and actuator. The volume of the chamber will determine the dose that is administered with each depression of the pump. The pump applies pressure to the formulation disposed within the chamber and causes the formulation to move through the actuator. The actuator is adapted to reduce the formulation into droplets capable of forming an aerosol spray for oral administration. The surfactant or other oral absorption enhancer is effective in reducing surface tension in providing a formulation capable of being reduced to droplet size by the actuator, forming an aerosol spray. The effectiveness of the delivery system is enhanced as the size of droplets is decreased to the point of where the particle has a minimum aerodynamic particle size distribution for effective transport. Typically, this is about 10 microns. A decreased droplet size translates to a higher surface area to be absorbed by the mucosa of the intra-oral cavity. With the propellant device, a chamber, valve, and actuator are also used. The formulation is pressured within the chamber. Depression of the valve causes pressure to be released so that the formulation moves through the actuator. Again, the actuator is adapted to reduce the formulation into droplets for oral administration. The surfactant or other oral absorption enhancer is effective in providing a formulation capable of being reduced to droplet size by the actuator.

The following examples will serve to further typify the nature of the invention but should not be construed as a limitation on the scope thereof, which is defined by the appended claims.

EXAMPLE 1

| Ingredients | % w/w |
|---|---|
| Pharmaceutical Agent<br>Insulin | 0.5 |
| Oral absorption enhancer<br>Surfactant | 1.2 |
| Carrier-solvent | |
| Tris-base | 0.48 |
| Ethanol | 20 |
| | 22.18 |
| Balance propellant | 77.82 |
| | 100 |

The ingredients are thoroughly mixed to form a solution. The solution is placed within a container of a propellant dispenser and administered orally to provide insulin to a patient in need thereof. The 0.5% insulin solution is effective in administering 17 units ("International Units" or "U.I.'s") to a patient per dose when a 150 microliter p-MDA™ is used.

EXAMPLE 2

| Ingredients | % w/w |
|---|---|
| Pharmaceutical Agent Fentanyl Citrate | 0.5 |
| Oral absorption enhancer Surfactant | 1.2 |
| Carrier-solvent Ethanol | 20 |
| | 21.7 |
| Balance propellant | 78.3 |
| | 100 |

The ingredients are thoroughly mixed to form a solution. The solution is placed within a container of a propellant dispenser and administered orally to provide pain relief to a patient in need thereof. The formulation is effective in treating patients suffering from pain associated with cancer and chemotherapy.

EXAMPLE 3

A bioavailability study was performed in a rat model, and the results are shown in FIG. 1. Plot A of FIG. 1 reflects a formulation containing 30 units (international units or "I.U.'s") of Bovine insulin. To achieve a dose of 30 units, the formulation may be prepared essentially as described above in Example 1, but using about 1% of the insulin. As can be seen, the formulation produced a 45% decrease in blood glucose over 90 minutes post administration of the insulin formulation. The decrease in blood glucose following administration was linear up to 90 minutes post dosing. Control formulations were administered and no decrease in blood glucose was observed. Plot B, for example, reflects a control comprising no active ingredient (no insulin) and no formulation according to the invention. Plot C reflects a control comprising the inventive formulation but without the active ingredient. Plot D reflects a control comprising the active ingredient but without the inventive formulation. This bioavailability study demonstrated that the method of preparation and composition of the formulation was effective in delivering the insulin to the patient and enabling a significant reduction in blood glucose level with an intra-oral delivery.

EXAMPLE 4

Insulin formulation and adapted for use in a pMDA, using 0.5% highly-purified porcine insulin. The lyophilized human insulin was dispersed along with tris-base (introducing initially at about 0.48) and Brij 98 (0.9%) (as a dispersing aid) and absorption enhancers (sodium lauryl sulfate at 1.2%) and surfactants in hydrofluoroalkane (HFA 134a) propellant in the presence of ethanol (20%). Here, the Brij surfactant comprises a formulation surfactant for increasing the formulation miscibility. The dose delivery through-the-valve (DDV) (e.g., of the pMDA) was analyzed by HPLC for insulin potency assay and degradation products. The finished pMDA units were stored at room temperature, and the DDV was determined at initial, 1, 2, 3, 4 and 14 months in order to follow the dosing consistency and chemical stability of insulin throughout the storage period. The formulation was administered to the intra-oral cavity of two humans. Two actuations were delivered into the intra-oral cavity of the two humans for each dose. Aliquots of blood were collected periodically in the next two hours following dosing. Hypoglycemic effect was measured as the percent change in blood glucose concentration compared with the baseline.

Stability tests revealed that the prepared insulin pMDA units delivered 32 to 38 IU per actuation, and DDV remained consistent after four months storage. In addition, no desamido insulin peak was detected for either the initial DDV sample or the 1,2,3 or 4 month stability DDV sample, indicating that no significant insulin degradation occurred in the product during the pMDa preparation process or the four-month stability storage period. The human study showed that the blood glucose level in humans started to decrease 20 minutes after administration of two actuations from the pMDA into the intra-oral cavity of humans, and a 30% decrease in the blood glucose level was observed between 40 and 100 minutes after dosing. The blood glucose level returned to baseline in 2 hours following the initial dosing. The results are plotted in FIG. 2.

EXAMPLE 5

A formulation was prepared essentially as in Example 4, except a human recombinant insulin at about 1% was used and the concentration of HFA decreased to make up the difference. The formulation was administered to two healthy male human volunteers (RM and ML). A baseline blood glucose level was established for each volunteer prior to the experiment. After fasting overnight, each volunteer was administered insulin pMDA into the intra-oral cavity. The glucodynamic effects were monitored for 5 hours following a 12-hour fast and the actuation of the pMDa. The percent change in blood glucose level from the baseline was established as a function of time to demonstrate the hypoglycemic effect.

Significant hypoglycemic effects were observed in this human study. FIGS. 3 and 4 are graphs plotting the glucose levels in the human subjects as a function of time, wherein each graph relates to a different subject. FIG. 3 pertains to subject "RM" after a single actuation of the pMDA. As can be seen, the glucose levels decrease along a basically linear plot for up to 300 minutes (five hours) after the single actuation. FIG. 4 pertains to subject "ML", also after a single actuation. Although the glucose levels are more varied, overall a generally downward trend is reported. In each case, the blood glucose level decreased sharply in the first 20 minutes after dosing, and the maximum hypoglycemic effect was observed between 100 and 150 minutes post dosing.

As can be seen, a stable propellant-driven pMDa formulation was developed for intra-oral delivery of insulin. Intra-oral delivery of insulin employing a pMDA formulation for treating diabetes has been established as feasible in this study. The administration was user friendly (no bad taste or chilled throat). In addition, administration of the formulation resulted in lowering glucose levels substantially below baseline levels.

EXAMPLE 6

Two formulations containing fentanyl citrate were prepared, wherein one formulation (identified as 12A) was prepared in accordance with Example 2, above, and the second formulation (12B) was prepared as per Example 2, with the exception that in 12B, water used as the solvent carrier in place of ethanol. The formulations were administered at pre-determined doses to six different rats and righting reflex was monitored at six different time intervals. Two rats under the same formulation lost their righting reflex, both at similar actuation intervals and after consecutive doses, and both regained righting reflexes within thirty-four minutes. One of these rats had been administered its dose by means of spray actuation and one by pipette. The second formulation containing the aqueous base (12B) did not appear to have a significant effect on either of the two rats administered (spray only) with it, as the righting reflex was regained in a short amount of time.

The procedure applied in this experiment was as follows: The rates were selected and weighed. One formulation was administered to each rat at a predetermined dose, the time was noted, and a time clock was begun. Each rat was monitored for loss of righting reflex or other signs of somnolence at 5, 10, 15, 30, 60, 120 minutes. The time was marked when the righting reflex was gone. If righting reflex was not gone in 30 minutes, the rat was re-dosed with 2 actuations and monitored as in time intervals as noted immediately above. The time when righting reflex returned was marked.

The data and results are reported below in Tables I, II, and II:

TABLE I

Formulation 12B

| Rat # | 5 min. | 10 min. | 15 min. | 30 min. | 60 min. | 120 min. |
|---|---|---|---|---|---|---|
| 632 | Intact | intact | Intact | Intact | Intact | intact |
| 633 | Intact | intact | Intact | Intact | Intact | intact |

TABLE II

Formulation 12A

| Rat # | 5 min. | 10 min. | 15 min. | 30 min. | 60 min. | 120 min. |
|---|---|---|---|---|---|---|
| 634 | Intact | Intact | Intact | Intact | intact | intact |
| 635 | Intact | Intact | Gone | Gone | Intact | intact |

TABLE III

Formulation 2A/50 µg dose administered by pipette

| Rat # | 5 min. | 10 min. | 15 min. | 30 min. | 60 min. | 120 min. |
|---|---|---|---|---|---|---|
| 636 | Intact | Intact | Gone | Gone | sleepy | sleepy |
| 637 | Intact | Intact | Intact | Sleepy | sleepy | sleepy |

As can be seen, all rats maintained righting reflex for intervals up to 30 min. with one actuation and, therefore, the above data reflects intervals with two actuations administered. Rats 636 and 637 received 90 microliters (one actuation) and 180 microliters (two actuations) of formulation 12A fentanyl citrate by pipette. The remaining subjects received the fentanyl citrate by spray actuations. The two rats (635 and 636) that lost righting reflex remained sleepy and weak after righting reflex again became intact at 60 and 120-minute intervals. Both of these rats were given formulation 12A, however, Rat 635 received the formulation by spray and Rat 636 received the formulation by pipette. The formulation was proven effective as well as both methods of administration. Rat 637 also began showing signs of somnolence at 15, 30, and 60-minute intervals although righting reflex remained intact. There were no signs of somnolence in either of the two rats that received the 12B formulation.

Thus, formulation 12A effected three of the four rats at high levels of fentanyl citrate in relation to this study. Because both rats received fentanyl by different means, the two forms of administration (spray and pipette) proved to be equally effective. After 30 minutes administering one actuation at the specified intervals and more than 15 minutes administering two actuations of the fentanyl citrate formulation, a response was manifested in the animals receiving formulation 12A. Formulation 12B did not effect either of the two rats that received it, and thus, an alcoholic-based system was preferred over an aqueous-based system in this instance.

We claim:

1. A substantially nonaqueous formulation for intra-oral delivery of at least one pharmaceutical agent to a patient comprising a solid or liquid dispersion comprising an effective amount of the pharmaceutical agent and at least one of (i) an orally-acceptable oral-absorptive enhancer operable to modify the absorptive surface of the targeted intra-oral membrane and enhance bioavailability of the pharmaceutical agent across the membrane and (ii) a formulation surfactant at least sufficient to increase the miscibility of the pharmaceutical agent, in an orally-acceptable nonaqueous carrier-solvent.

2. The formulation according to claim 1 in which the pharmaceutical agent is selected from the group consisting of a glucocorticoid steroid, testosterone, stanozolol, barbiturates, benzodiazepines, a sedative-hypnotic, nitroglycerine, an analgesic and a peptide or protein having a molecular weight up to about 50,000 Daltons, or an orally administerable non-toxic salt of said pharmaceutical agent.

3. The formulation according to claim 2 in which the peptide or protein is calcitonin, insulin, GLP, HGH, or leuprolide.

4. The formulation according to claim 2 in which the analgesic is ketorolac, oxandrolone, morphine, fentanyl, codeine, or a pharmaceutically effective salt thereof.

5. The formulation according to claim 2 in which the glucocorticosteroid is secreted from a group consisting of dexmethasone, prednisolone and prednisone.

6. The formulation according to claim 2 in which the barbiturate is seconal.

7. The formulation according to claim 1 in which the pharmaceutical agent is present in an amount of about 0.001 to 25% by weight of the composition.

8. The formulation according to claim 1 in which the oral-absorption enhancer is selected from the group consisting of hydroxypropyl-beta-cyclodextrin, benzalkonium chloride, benzethonium chloride, polysorbate 80, sodium lauryl sulfate, polyoxyethylene ethers of aliphatic alcohols, polyoxyethylene derivatives of fatty acid partial esters of sorbitol anhydride, and polyoxyalkylene block copolymers.

9. The formulation according to claim 1 in which the oral-absorption enhancer is present in an amount of about 0.1 to 20% by weight.

10. The formulation according to claim 1 in which the carrier solvent is selected from the group consisting of ethanol, glycerol, glycol, propylene glycol, polyethylene glycol, sorbitol, vitamin E, derivatives of vitamin E, and polyvinylpyrrolidone.

11. The formulation according to claim 1 in which the carrier solvent is present in an amount of about 0.5 to 50% by weight of the composition.

12. The formulation according to claim 1 in which the formulation surfactant reduces the pharmaceutical agent to an average droplet size of from about 10 to about 200 microns.

13. The formulation according to claim 1 further comprising a propellant.

14. The formulation according to claim 13 in which the propellant is selected from the group consisting of hydrofluoroalkane, propane, HFA-134A, HFA-152A, HFA-227, freon 12, freon 13, butane, and carbon dioxide.

15. The formulation according to claim 14 in which the propellant is present in an amount of from 20 to 95 % by weight.

16. The formulation according to claim 1 in which the pharmaceutical agent comprises insulin.

17. The formulation according to claim 1 in which the pharmaceutical agent comprises fentanyl citrate.

18. A substantially nonaqueous fluid formulation according to claim 1 effective for intra-oral delivery of at least one pharmaceutical agent to a patient, the formulation comprising an effective amount of the pharmaceutical agent mixed with at least one oral-absorption enhancer operable to modify the adsorptive surface of the targeted intra-oral membrane and improve absorption of the pharmaceutical agent across the oral mucosa, ethanol, a substantially nonaqueous propellant operable to deliver the pharmaceutical agent to the mucosa of the patient's intra-oral cavity, and a formulation surfactant operable to increase miscibility of the pharmaceutical agent, oral-absorption enhancer, ethanol, and propellant and reduce the pharmaceutical agent to an average droplet size of less than 200 microns.

19. A nonaqueous formulation as recited in claim 1 consisting essentially of a solid or liquid dispersion containing (i) about 0.1 to about 10% by weight of a pharmaceutical agent; (ii) about 0.1% to about 10% by weight oral-absorptive enhancer selected from the group consisting of hydroxypropyl-beta-cyclodextrin, benzalkonium chloride, benzethonium chloride, polysorbate 80, sodium lauryl sulfate, polyoxyethylene ethers of aliphatic alcohols, polyoxyethylene derivatives of fatty acid partial esters of sorbitol anhydride, and polyoxyalkylene block copolymers; (iii) about 5 to about 50% of a carrier solvent select from the group consisting of ethanol, glycerol, glycol, propylene glycol, polyethylene glycol, sorbitol, vitamin E, derivatives of vitamin E, and polyvinylpyrrolidone, (iv) about 20 to about 90% by weight of a fluorocarbon or a chlorofluorocarbon propellant and optionally (i) an additional surfactant to increase miscibility selected from the group consisting of ethers of aliphatic alcohols, polyoxyethylene derivatives of fatty acid partial esters of sorbitol anhydride, and polyoxyalkylene block copolymers; and (ii) up to about 5% of stabilizer or preservative selected from the group consisting of lactic acid, citric acid, benzoic acid, benzyl alcohol, thimerosal, phenylethyl alcohol, benzethonium chloride, methyl paraben, ethyl paraben, butyl paraben and propyl paraben.

20. A formula according to claim 19 wherein the average droplet size is from about 10 to about 200 microns.

21. A formula according to claim 19 in which the pharmaceutical agent comprises insulin.

22. A formulation according to claim 19 wherein the carrier solvent is ethanol.

23. A system for intra-oral delivery to a patient of a pharmaceutical agent comprising:

a substantially nonaqueous fluid formulation for intra-oral delivery of at least one pharmaceutical agent to a patient comprising a solid or liquid dispersion substantially free of reversed micelles comprising an effective amount of the pharmaceutical agent and at least one of (i) an orally-acceptable oral-absorption enhancer operable to modify the absorptive surface of the targeted intra-oral membrane and enhance bioavailability of the pharmaceutical agent across the membrane and (ii) a formulation surfactant at least sufficient to increase the miscibility of the pharmaceutical agent, in an orally-acceptable nonaqueous carrier-solvent; and, a mechanical assembly operable for dispensing the formulation to the mucosa of the intra-oral cavity of the patient, wherein the mechanical assembly includes an aerosolizing device and the formulation is disposed within the mechanical assembly and emitted therefrom in a spray caused by the aerosolizing device.

24. The system of claim 23 in which the mechanical assembly comprises a pump device.

25. The system of claim 23 in which the mechanical assembly comprises a propellant device.

26. A system for treating a patient with a pharmaceutical agent comprising (i) a substantially nonaqueous fluid formulation for intra-oral delivery of at least one pharmaceutical agent to a patient comprising a solid or liquid dispersion substantially free of reversed micelles comprising an effective amount of the pharmaceutical agent and at least one of (a) an orally-acceptable oral-absorption enhancer operable to modify the absorptive surface of the targeted intra-oral membrane and enhance bioavailability of the pharmaceutical agent across the membrane and (b) a formulation surfactant at least sufficient to increase the miscibility of the pharmaceutical agent, in an orally-acceptable nonaqueous carrier-solvent; and, (ii) a mechanical assembly operable for dispensing the formulation to the mucosa of the intraoral cavity, the mechanical assembly having an aerosolizing device for reducing the formulation to a spray.

27. A method for administering a pharmaceutical agent to a patient comprising providing the system of claim 26 and spraying the formulation into the patient's intra-oral cavity.

* * * * *